United States Patent [19]

Gary et al.

[11] 4,062,938

[45] Dec. 13, 1977

[54] ALUMINUM HYDROXYBROMIDE ANTIPERSPIRANT COMPOSITIONS

[75] Inventors: Herbert H. Gary, Edison; Chung T. Shin, Livingston, both of N.J.

[73] Assignee: Bristol-Myers Company, New York, N.Y.

[21] Appl. No.: 415,575

[22] Filed: Nov. 14, 1973

Related U.S. Application Data

[63] Continuation-in-part of Ser. No. 82,784, Oct. 21, 1970, abandoned.

[51] Int. Cl.$^2$ .................................................. A61K 7/38
[52] U.S. Cl. ............................................. 424/47; 424/68
[58] Field of Search ................................... 424/47, 68

[56] References Cited

U.S. PATENT DOCUMENTS

| | | | |
|---|---|---|---|
| 1,621,528 | 3/1927 | Ellis | 424/154 |
| 2,196,016 | 4/1940 | Huehn et al. | 23/123 X |
| 3,359,169 | 12/1967 | Slater, Jr. et al. | 424/68 |
| 3,420,932 | 1/1969 | Jones et al. | 424/68 X |
| 3,476,509 | 11/1969 | Jones | 23/50 R |
| 3,511,864 | 5/1970 | Ugelow et al. | 260/448 AD |

*Primary Examiner*—Dale R. Ore
*Attorney, Agent, or Firm*—David J. Mugford; George A. Mentis; John A. Caruso

[57] ABSTRACT

An antiperspirant composition comprising a physiologically acceptable carrier e.g. ethyl alcohol or ethyl alcohol and a polyhydric compound of formula $R(OR')_nOH$ and about 10 to 45% by weight of an aluminum hydroxybromide; R in said formula is H or lower alkyl, R' is polymethylene having 2 to 4 carbon atoms and n is 1 to 3.

12 Claims, No Drawings

ALUMINUM HYDROXYBROMIDE ANTIPERSPIRANT COMPOSITIONS

RELATED CASES

This application is a continuation-in-part of application Ser. No. 82,784, filed Oct. 21, 1970, now abandoned.

This invention related to antiperspirant compositions and, more particularly, to antiperspirant compositions containing an aluminum hydroxybromide as an active antiperspirant ingredient. It also concerns a method for inhibiting perspiration by applying to subjects a composition containing an effective antiperspirant amount of an aluminum hydroxybromide.

Aluminum hydroxychloride has been long used in the prior art as an antiperspirant. However, it has one particular disadvantage in that it has a relatively low solubility in solvents that are ordinarily employed in these compositions and particularly in aerosol systems. Thus, for example, aluminum hydroxychloride is soluble in ethyl alcohol only to the extent of 10%. In aerosol systems this solubility is effectively reduced, therefore reducing its concentration in the final composition. This puts a severe limit on the effectiveness of this material.

It has been discovered that effective antiperspirant compositions may be prepared by using an aluminum hydroxybromide as the effective antiperspirant agent. It has been unexpectedly found that aluminum hydroxybromides, (and particularly the aluminum hydroxybromides corresponding to the formula $Al_2(OH)_5Br$ and its hydrates) are soluble in ethyl alcohol up to about 45%. It has further been found that a portion of the ethyl alcohol can be replaced by a polyhydric alcohol compound without deleterously effecting the solubility of the aluminum hydroxybromide in the solvent system. In this form the aluminum hydroxybromide is conveniently incorporated in an aerosol system. It has also been unexpectedly found that $Al_2(OH)_5Br$ in these systems are less corrosive to aerosol cans than systems that one could prepare with even the lower and less effective concentration of $Al_2(OH)_5Cl$.

It is accordingly an object of the present invention to provide a composition and method for inhibiting perspiration using an effective amount of an aluminum hydroxybromide as the active antiperspirant ingredient.

It is another object of this invention to provide an effective antiperspirant which has good solubility in alcohol and in alcohol-polyhydric alcohol compound solvent systems.

It is a further object of this invention to provide a composition of the above character incorporated in an aerosol system.

It is still a further object of the present invention to provide through the use of aluminum hydroxybromide or its hydrates an antiperspirant composition containing relatively high concentrations of active antiperspirant material (i.e., higher than those commonly found in the prior art composition) thus making available more effective antiperspirant products.

Other and more detailed objects will be apparent from the following description and claims.

A variety of aluminum hydroxybromides are useful for the purposes of the present invention. Of special interest are the aluminum hydroxybromides believed to be of the general formula:

$$Al_2(OH)_xBr_{(6-x)}$$

and their hydrates (in which $x$ is a number from 1 to 5). Compounds falling within this definition are described in U.S. Pat. No. 2,196,016 and particularly Example 2 in which the bromide to aluminum ratio is 3:2 and which corresponds to the formula $Al_2(OH)_3Br_3$. Similarly, compounds corresponding to the formula $Al_2(OH)_5Br$ and its hydratees e.g. $Al_2(OH)_5Br$ 2.5 $H_2O$ exemplary other aluminum hydroxybromides which can be suitably employed. The latter can be prepared by mixing metallic Al (41.5 parts), HBr (24 parts), $AlBr_3$(53 parts) in water (100 parts).

The quantities of the aluminum hydroxybromide that may be utilized in the compositions of the present invention may vary considerably. All that is required is that they contain an amount sufficient to have effective antiperspirant activity. However, in general, to take full advantage of the effectiveness of the aluminum hydroxybromide the compositions will contain from 10.0% to 45% by weight of an aluminum hydroxybromide and preferably from 15 to 30% by weight based on the total weight of the composition.

Another feature of the present invention is the unexpected discovery that aluminum hydroxybromides can be very effectively applied from a solvent system containing ethyl alcohol because of their extremely good solubility in ethyl alcohol containing solvent systems. For certain purposes, it has been found that a portion of the ethyl alcohol solvent may be advantageously replaced by a polyhydric alcohol compound. In this case, the polyhydric alcohol compound will constitute between 20 to 80% by weight of the solvent system, the remainder being essentially ethyl alcohol.

As used herein the term polyhydric alcohol compound means polyhydric alcohols, (either monomeric or polymeric) and this corresponding mono alkyl ethers. More particularly, these polyhydric compounds are defined by the formula:

$$R(OR')_nOH$$

wherein R is hydrogen or lower alkyl (i.e. from 1 to 6 carbon atoms and preferably 1 to 4 carbon atoms); R' is polymethylene having from 2 to 4 carbon atoms and $n$ is a number from 1 to 3. By way of illustrating specific compounds that are useful for the present purposes, mention may be made of propylene glycol, di-propylene glycol, and the Carbitols i.e. compounds of formula:

$$R'''OCH_2CH_2OCH_2CH_2OH$$

in which R''' is methyl, ethyl, propyl and butyl. However, the preferred polyhydric alcohol compound is propylene glycol.

In a preferred form of this invention the compositions take the form of aerosol preparations. In these cases the aluminum hydroxybromide is prepared in the form of a concentrate in a solvent system comprising ethyl alchol and e.g. propylene glycol. This is charged into an aerosol can which is then filled with propellant.

In light of the fact that the aluminum hydroxybromides have good solubility in the contemplated solvent systems, there is no need to add water to the composition. They can therefore constitute substantially non-aqueous or anhydrous systems.

In Table I below the various ranges of the essential components of the compositions of this invention are summarized:

TABLE I

| COMPONENTS | % by weight of total composition | |
| --- | --- | --- |
|  | Non-Aerosol | Aerosol |
| Aluminum Hydroxybromide | 10 to 45 | 10 to 45 |
| Ethyl Alcohol | 20 to 80 | 20 to 80 |
| Polyhydric Alcohol Compound | 0 to 80 | 0 to 80 |
| Propellant |  | 5 to 70 |

In preparing aerosol compositions encompassed in the present invention any of a variety of propellants may be used e.g. gasses or low boiling liquids. It is preferred that the propellant utilized be a non-toxic, liquid propellant. It may be flourinated or a fluorocholorinated lower saturated aliphatic hydrocarbon, and preferably a halogenated alkane containing not more than 2 carbon atoms and at least 1 fluorine atom, or mixtures thereof. The preferred halogenated lower alkane compounds may be represented, generally, by the formula: $C_mH_nCl_yF_z$, wherein $m$ is an integer less than 3, $n$ is an integer or zero, $y$ is an integer or zero, and $z$ is an integer, such that $n + y + z = 2m + 2$.

It may also be a liquified hydrocarbon gas, e.g. butane, isobutane, propane, etc. These may be used alone or admixed with each other. In addition, they may also be employed in admixture with the haolgenated propellants mentioned above.

The propellants should preferably possess a boiling point of less than 75° F at 760 mm. pressure. Typical examples of useful propellants are dichlorodifluoromethane ("Freon 12"), dichlorotetrafluoroethane ("Freon 114"), $CClF_2-CClF_2$, trichloromonofluoromethane ("Freon 11"), dichloromonofluoromethane ("Freon 21"), monochlorotrifluoromethane ("Freon 13") or $CCl_2F-CClF_2$ ("Freon 113"). Propellants with improved vapor pressure characteristics may be obtained by using certain mixtures of these compounds, e.g., "Freon 11" and "Freon 12" or "Freon 21" and "Freon 114". For example, dichlorodifluoromethane, which has a vapor pressure of about 70 pounds per square inch gauge and 1,2 dichloro-1,1,2.2-tetrafluoroethane ("Freon 114"), with a vapor pressure of about 13 pounds per square inch gauge at 70° F may be mixed in various proportions to form a propellant having an intermediate vapor pressure which is well suited for use in relatively low pressure containers.

It is desired that the vapor pressure of the propellant employed shall itself be between about 25 and 65 pounds per square inch gauge at 70° F, and preferably between about 30 and 40 pounds per square inch gauge at that temperature. A one-component propellant defined for use in the composition was found to give a composition with gauge pressures in the range of 55 to 65 pounds per square inch at 70° F, which are usable safely with metal containers. The two-component propellants, such as equal weight mixtures of "Freon 12" and "Freon 11", were found to give gauge pressures in the range of 20 to 40 pounds per square inch at 70° F, which are usable safely with specially reinforced glass containers.

In addition to the principle ingredients described above, the compositions of the present invention may also contain other components commonly found in antiperspirant composition. Thus, they may contain perfumes, coloring materials, bactericides, emollients, lubricants, etc.

In use the compositions of this invention are applied to skin area of subject where the perspiration is to be inhibited. Enough material is applied to the skin to deposit an effective antiperspirant quantity of material. This will ordinarily be in the range of about 10 to 600 milligrams of the aluminum hydroxybromide and preferably about 20 to 100 milligrams of this material.

The following examples are further illustrative of the present invention. It is to be understood, however, that the invention is not limited here. All percentages are given in percent by weight unless otherwise specified.

EXAMPLES 1-3

| Component | Liquid Preparations (Non-Aerosol) | | |
| --- | --- | --- | --- |
|  | Example 1 | Example 2 | Example 3 |
| $Al_2(OH)_5Br\ 2\ H_2O$ | 30 gms→ | → | → |
| Ethyl Alcohol | 35 gms | 20 gms | 50 gms |
| Propylene Glycol | 35 gms | 50 gms | 20 gms |

In preparing these compositions, the propylene glycol was heated to about 55° C and the alcohol and aluminum hydroxybromide was added. Then materials were mixed and gave a clear solution. These were screened for antiperspirant activity by forearm screening and found to be active.

These solutions can be packaged in conventional roll-on or dab-o-matic applicators. When ¼ to 1 gram of the above compositions are applied (i.e. 50-100 mg. of $Al_2(OH)_5Br$) they will be effective antiperspirants.

EXAMPLE 4

Aerosol Preparation

Seventy-five parts of propylene glycol and 25 parts of ethyl alcohol were mixed together. To 75 grams of this solution 25 grams of the aluminum hydroxybromide of formula $Al_2[OH]_5Br\ 2.5\ H_2O$ were added. Eighty grams of this concentrate was added to an aerosol can which was then charged with 20 grams of Freon 12 (dichlorodifluoromethane).

Fifty to 100 milligrams of $Al_2(OH)_5Br\ 2.5\ H_2O$ deposited on the skin from the above composition is an effective antiperspirant.

EXAMPLE 5

Aerosol Perparation

The procedure of Example 4 was followed excepting that the concentrate was prepared having the following composition:

Propylene Glycol: 67.50 parts
Ethyl Alcohol: 22.50 parts
$Al_2[OH]_5Br\ 2.5\ H_2O$: 30.00 parts This concentrate (80 grams) was charged into an aerosol can to which was then added 20 grams of Freon 12 propellant.

Fifty to 100 milligrams of $Al_2(OH)_5Br\ 2.5\ H_2O$ deposited on the skin from the above composition will be an effective antiperspirant.

EXAMPLE 6

Aerosol Preparation

The procedure of Example 4 was followed excepting that the concentrate used has the following forumla:

| Ethyl Alcohol | 27.5 parts |
| --- | --- |

| | |
|---|---|
| -continued | |
| Al$_2$(OH)$_5$Br | 30.0 parts |
| Propylene Glycol | 62.5 parts |
| | 120.0 |

EXAMPLE 7

The procedure of Example 4 is followed in all respects excepting that in place of the 10 grams of Al$_2$(OH)$_5$Br 2.5 H$_2$O, an equivalent amount of the aluminum hydroxybromide prepared in accordance with Example 2 of U.S. Pat. No. 2,196,016 is employed.

Fifty to 100 milligrams of this aluminum hydroxybrodmide deposited on the skin from this composition will be an effective antiperspirant.

EXAMPLE 8

Aerosol Preparation

Using the procedure of Example 4 the following composition is prepared:

| | |
|---|---|
| Al$_2$(OH)$_5$Br 2.5 H$_2$O | 25.0% |
| Propylene Glycol | 35.0% |
| Ethyl Alcohol | 20.0% |
| Freon 12 | 20.0% |

EXAMPLE 9

The procedure of Example 4 is followed excepting that the concentrate used has the following formula:

| | |
|---|---|
| Propylene Glycol | 20.00 parts |
| Ethyl Alcohol | 50.00 parts |
| Al$_2$[OH]$_5$Br 2.5 H$_2$O | 30.00 parts |

EXAMPLE 10

The procedure of Example 4 is followed excepting that the concentrate used has the following formula:
Ethyl Alcohol: 45.0%
Al$_2$(OH)$_5$Br . 2.5 H$_2$O: 30.0%
Propylene Glycol: 25.0%

EXAMPLE 11

Using the procedure of Example 4 the following composition is prepared:
Al$_2$[OH]$_5$Br 2.5 H$_2$O: 25.0% Propylene Glycol: 20.0%
Ethyl Alcohol: 35.0% Freon 12: 20.0%

What is claimed is:

1. An antiperspirant composition comprising a solvent system containing about 20% to 80% by weight of the total composition of ethyl alcohol and about from 0% to 80% by weight of the total composition of a polyhydric compound; and about from 10 to 45% by weight of an aluminum hydroxybromide or hydrates thereof; said aluminum hydroxybromide being of formula:

$$Al_2(OH)_xBr_{(6-x)}$$

wherein
x is a number from 1 to 5;
and said polyhydric compound being of formula:

$$R(OR')_nOH$$

wherein R is hydrogen or alkyl having from 1 to 6 carbon atoms;
R' is polymethylene having 2 to 4 carbon atoms; and
n is a number from 1 to 3.

2. A composition according to claim 1 wherein said polyhydric compound is present in an amoung of from about 20% to 80% by weight of the total solvent.

3. A composition according to claim 2 wherein said polyhydric compound is propylene glycol.

4. A composition according to claim 1 wherein said aluminum hydroxybromide is present in said composition in an amount of from about 15 to 30% by weight of the total composition.

5. A composition according to claim 1 wherein said aluminum hydroxybromide contains, 0, 2, or 2.5 moles of water of hydration.

6. A composition according to claim 1 wherein the aluminum hydroxybromide corresponds to formula of Al$_2$(OH)$_5$Br or hydrates thereof.

7. A composition according to claim 1 in the form of an aerosol composition including an aerosol propellant selected from the group consisting of normally gaseous halogenated lower alkanes, normally gaseous lower saturated aliphatic hydrocarbons containing up to four carbon atoms and mixtures thereof, said halogenated lower alkanes containing up to two carbon atoms and at least one fluorine atom.

8. A composition according to claim 7 in which the solvent system contains about 20% to 80% by weight of said polyhydric compound based on the weight of the solvent system.

9. A composition according to claim 8 wherein said polyhydric compound is propylene glycol.

10. A composition according to claim 9 wherein the propellant is present in an amount of about 5% to 7% by weight of the total composition.

11. A composition according to claim 10 wherein the aluminumn hydroxybromide corresponds to the formula Al$_2$(OH)$_5$Br or hydrates thereof.

12. A composition according to claim 11 in which the aluminumn hydroxybromide contains 0, 2, or 2.5 moles of water of hydration.

* * * * *